United States Patent [19]

Rakoutz

[11] 3,956,346
[45] May 11, 1976

[54] PROCESS FOR THE PREPARATION OF TRIMETHYL-BENZOQUINONE

[75] Inventor: Michel Rakoutz, Oullins, France

[73] Assignee: Rhone-Poulenc Industries, Paris, France

[22] Filed: Jan. 17, 1975

[21] Appl. No.: 542,003

[30] Foreign Application Priority Data

Jan. 21, 1974  France .............................. 74.01917

[52] U.S. Cl. ....................... 260/396 R; 260/621 H; 260/621 R
[51] Int. Cl.² ......................................... C07C 49/64
[58] Field of Search ................................ 260/396 R

[56] References Cited
UNITED STATES PATENTS 2,343,768  3/1944  Gibbs ............................. 260/396 R
3,700,701  10/1972  Dietl ............................... 260/396 R
3,795,708  3/1974  Rappen et al. ................... 260/396 R

*Primary Examiner*—Vivian Garner
*Attorney, Agent, or Firm*—Cushman, Darby & Cushman

[57] ABSTRACT

A process for preparing trimethylbenzoquinone is provided which does not involve the formation of a sulphonic acid intermediate which comprises oxidising 2,3,6-trimethyl-phenol directly with manganese dioxide in an aqueous solution containing sulphuric acid in an amount up to 40% by weight.

9 Claims, No Drawings

PROCESS FOR THE PREPARATION OF TRIMETHYL-BENZOQUINONE

The present invention relates to a process for the preparation of trimethyl-benzoquinone from 2,3,6-trimethyl-phenol.

Trimethyl-benzoquinone is an intermediate in the synthesis of trimethyl-hydroquinone, which is an important organic product used as a precursor of vitamin E; because of the ease with which 2,3,6-trimethyl-phenol can be obtained, it is a preferred starting material for the preparation of trimethyl-benzoquinone.

Various methods for the preparation of trimethyl-benzoquinone from 2,3,6-trimethyl-phenol have been proposed, amongst which the most satisfactory is the oxidation of 2,3,6-trimethyl-phenol by means of an inorganic oxidising agent in a sulphuric acid medium. Thus, trimethyl-benzoquinone has been synthesised by the oxidation of 2,3,6-trimethyl-phenol by means of sodium dichromate dissolved in concentrated sulphuric acid [see, for example, Smith et al., Journal of Organic Chemistry, 4 320 (1939)], but the yield is only 50%.

The preparation of p-benzoquinones which are substituted, particularly by methyl groups in the o- and o'-positions and optionally in the m- and/or m'-positions, has been proposed, by means of a process which involves prior sulphonation of the corresponding phenol by means of concentrated sulphuric acid followed by oxidation by means of chromic acid or pyrolusite (see, for example, German Pat. No. 1,022,209). In addition to the low yields (35 – 69% of theory), this process requires the reaction to proceed via the sulphonic acid as an intermediate.

For the purpose of improving the yields, it has been proposed to carry out the sulphonation of 2,3,6-trimethyl-phenol by means of concentrated sulphuric acid followed by oxidation by means of sodium dichromate or manganese dioxide (see French Pat. No. 2,051,407) in the presence of solvents which are immiscible with water. The yield is improved but the process still requires a prior sulphonation step, using concentrated sulphuric acid in large amounts, and this poses corrosion problems which are increased by the presence of trimethylphenol-sulphonic acid which is itself very corrosive. Furthermore, this process necessarily involves the use of a solvent.

It is thus desirable to have available a process which makes it possible to prepare trimethyl-benzoquinone by direct oxidation of 2,3,6-trimethyl-phenol, in good yields.

According to the present invention there is provided a process which makes it possible to obtain trimethyl-benzoquinone starting from 2,3,6-trimethyl-phenol, without an intermediate sulphonation step, and this makes it possible to increase the productivity of the equipment and to simplify the industrial manufacture of the desired product. The process of the present invention comprises directly oxidising 2,3,6-trimethyl-phenol by means of manganese dioxide in an aqueous solution containing sulphuric acid in an amount not exceeding 40% by weight.

It has been found, unexpectedly, that under these conditions the yields of trimethyl-benzoquinone are approximately 80% and that they decrease rapidly when the concentration of sulphuric acid increases beyond 40%. It has also been found that under the specified conditions a phenol-sulphonic acid is not formed as an intermediate.

The nature of the manganese dioxide used as the oxidising agent is not critical and it is possible to use pure manganese dioxide or natural oxides such as pyrolusite. Whatever the nature of the manganese dioxide, the amount of manganese dioxide used is generally approximately 2 mols per mol of 2,3,6-trimethyl-phenol employed. It is however possible to use amounts which are less, or greater, than the stoichiometric requirements. Thus the $MnO_2$/2,3,6-trimethyl-phenol molar ratio can suitably vary from 1.8 to 3, preferably from 2.1 to 2.5.

The concentration of sulphuric acid can vary within rather wide limits below the maximum of 40%, it can be as low as, for example, 5% by weight. Aqueous solutions of sulphuric acid, the concentration of which is from 5 to 30% by weight are preferably employed.

The amount of sulphuric acid used should generally be at least 1 mol per mol of manganese dioxide employed. It is possible to use a considerable excess such that the amount of sulphuric acid can be as much as, for example, 4 mols per mol of manganese dioxide. For reasons of convenience and in order to ensure sufficient productivity of the equipment, it generally suffices to employ about 2 mols of sulphuric acid per mol of manganese dioxide.

Where appropriate, the concentration of sulphuric acid can be kept at its original value, or within the limits defined above, for the duration of the reaction by adding concentrated sulphuric acid as the latter is consumed.

The oxidation is suitably carried out at a temperature of from 10°C to the reflux temperature of the reaction mixture. In general, a temperature from 20° to 80°is very suitable.

The method by which the reagents are introduced is not critical, but it is nevertheless advantageous to add 2,3,6-trimethyl-phenol, in solid form or in the molten state, gradually to the aqueous solution of sulphuric acid containing manganese dioxide in suspension.

Trimethyl-benzoquinone can be isolated from the reaction mixture by steam distillation or by extraction using a solvent which is immiscible with water, such as benzene, toluene, xylene, chlorobenzene, n-hexane, ligroin, cyclohexane, carbon tetrachloride, chloroform or methyl isobutyl ketone.

The trimethyl-benzoquinone thus obtained can be reduced by means of the usual processes. Thus it is possible to effect catalytic hydrogenation in an aromatic solvent such as toluene, pseudo-cumene or the xylenes. The usual catalysts for hydrogenating quinones can be used, such as Raney nickel, Raney cobalt or noble metals (palladium, platinum, ruthenium or rhodium) which may or may not be desposited on supports such as alumina, silica, pumice stone or the different varieties of carbon.

It is also possible to carry out the reduction of tri-methyl-benzoquinone using any known method for the reduction of quinones, in particular zinc in an acid medium or alkali metal hydrosulphites.

The reagents and the working conditions of the process of the present invention are very suitable for continuous operation.

The following Examples further illustrate the present invention.

EXAMPLE 1

A 20% strength aqueous solution (200 cc.) of sulphuric acid (0.40 mol) and pyrolusite (22 g.), containing 89.5% by weight of $MnO_2$ (0.23 mol), are introduced into a 250 cc. three-necked flask equipped with a mechanical stirrer, a reflux condenser, a heated-lagged dropping funnel and a thermometer.

The reaction mixture is heated with stirring to 75°C and 2,3,6-trimethyl-phenol (13.3 g; 0.098 mol) held in the lagged dropping funnel is run uniformly into this mixture over the course of 40 minutes. During the addition, the temperature is kept between 70° and 75°C. The mixture is then heated at 70°–75°C for a further 25 minutes, with continuous stirring.

The mixture is allowed to cool to ambient temperature; chloroform (50 cc.) is then added and the solid residue is filtered off on sintered glass. The residue is washed on the filter with chloroform (4 times 50 cc.). The filtrate is extracted with chloroform (5 times 50 cc.). The chloroform phases are combined and made up to 500 cc. by adding chloroform.

The trimethyl-benzoquinone in the solution obtained is measured by UV spectrometry. For this purpose, a sample of solution (20 cc.). is taken and is then evaporated to constant weight. A residue (0.60 g.) is collected, in which trimethyl-benzoquinone (0.576 g., corresponding to 96% of the residue) is measured by UV.

A total of 11.6 g. of trimethyl-benzoquinone has thus been formed; this corresponds to a yield of 79% relative to the 2,3,6-trimethyl-phenol employed.

The quinone present in the remaining chloroform extract is reduced by concentrating the extract (to 100 cc.) and then treating it with sodium hydrosulphite (30 g.) in water (200 cc.); trimethyl-hydroquinone precipitates. The reaction mixture is filtered and the precipitate is washed on a filter with chilled water (4 times 50 cc.), drained and then dried to constant weight under the vacuum provided by a water pump. A precipitate (10.6 g.) containing pure trimethyl-hydroquinone (10.2 g) is thus obtained.

Trimethyl-hydroquinone (1 g.) is analysed by polarography in an ether extract of the filtrate after having evaporated it to dryness. Taking into account the sample removed for the UV measurement, 11.7 g of trimethyl-hydroquinone has been formed; this corresponds to a yield of 78.7% (relative to the phenol employed).

For comparison purposes, the following experiments in which the concentration of sulphuric acid was varied, were carried out.

Experiment A

An 80% strength by weight aqueous solution (50 cc.) of sulphuric acid (0.41 mol) and natural manganese dioxide (11 g.; 0.11 mol) are introduced into the apparatus described above.

The mixture is heated to 70°C, with stirring, and molten 2,3,6-trimethyl-phenol (6.8 g.; 0.05 mol) is run in over the course of 65 minutes. The reaction is exothermic and the temperature rises to 95°C. At the end of the addition, the reaction mixture is highly coloured.

Distilled water (200 cc.) is added and extraction is effected using benzene (4 times 50 cc.). The combined benzene phases are concentrated (to 50 cc.).

Unconverted 2,3,6-trimethyl-phenol (1.6 g.) is measured by gas phase chromatography and trimethyl-benzoquinone (170 mg.) is determined by polarography.

Experiment B

Natural manganese dioxide (11 g.; 0.11 mol) and a 50% strength aqueous solution (100 cc.) of sulphuric acid (0.51 mol) are introduced into the apparatus described above.

The mixture is heated to 72°C, with stirring, and molten 2,3,6,-trimethyl-phenol (6.7 g.; 0.049 mol) is run in over the course of 35 minutes. The temperature of the mixture is kept between 75° and 82°C. Heating at this temperature is then continued for 20 minutes.

The mixture is allowed to cool and benzene (50 cc.) is added. The reaction mixture is filtered and the precipitate is washed with benzene (3 times 50 cc.). The filtrate is extracted with benzene (4 times 50 cc.). The combined organic phases are concentrated (to 50 cc.) and the quinone is reduced by means of sodium hydrosulphite (15 g.) in distilled water (150 cc.).

After filtration, trimethyl-hydroquinone (2.8 g.), the purity of which, determined by polarography, is 80%, is recovered.

In the filtrate, trimethyl-hydroquinone (a further 360 mg.) is determined by polarography and unconverted 2,3,6-trimethyl-phenol (700 mg.) is determined by vapour phase chromatography.

A total weight of 2.6 g. of trimethyl-hydroquinone is obtained, the yield relative to the converted trimethyl-phenol being 38.8%.

Experiment C

An experiment similar to B insofar as the concentration of sulphuric acid is concerned is carried out, but no manganese dioxide is introduced.

The following reagents: 2,3,6-trimethyl-phenol (5 g.; 0.04 mol) and 50% strength sulphuric acid (175 g.; 0.9 mol) are introduced into a 250 cc. three-necked flask equipped with a mechanical stirrer and a thermometer.

The mixture is heated to 64° – 65°C by means of a thermostatically controlled bath and this temperature is maintained for 1 hour.

No precipitation of phenol-sulphonic acid is observed.

The reaction mixture is extracted directly with benzene (4 times 150 cc.). The benzene solution is dried over magnesium sulphate. After filtration, the solvent is evaporated to leave a dry residue.

A yellowish solid (5 g.) is recovered, the melting point of which is 62°C and which is identified by infrared spectroscopy as being 2,3,6-trimethyl-phenol.

It can thus be seen that the use of sulphuric acid of 50% concentration does not make it possible to sulphonate 2,3,6-trimethyl-phenol and that consequently the oxidation of the latter by means of manganese dioxide in sulphuric acid of 40% maximum concentration takes place without intermediate sulphonation.

EXAMPLE 2

A 20% strength aqueous solution (375 cc.) of sulphuric acid (0.76 mol) and pyrolusite (41 g.) (89.5% by weight of $MnO_2$) (0.42 mol) are introduced into a three-necked flask equipped as in Example 1.

The mixture is heated to 72°C, with stirring, and 2,3,6-trimethyl-phenol (25 g.; 0.184 mol) is run in over the course of 55 minutes, and the whole is then left for a further 25 minutes, with stirring, at 72°–75°C. The dropping funnel is then replaced by a curved tube extended by a condenser and a receiving vessel. The reflux condenser is replaced by an inlet for bubbling steam through the reaction mixture.

Trimethyl-benzoquinone is steam distilled in vacuo (150 mm Hg). The temperature of the reaction mixture is kept at 63°C by introducing steam. After 2½ hours of steam distillation, the mixture is brought back to atmospheric pressure and distillation is continued for a further 1 hour. A distillate (total volume = 1,920 cc.) is collected. The distillate is extracted with toluene (4 times 100 cc.). The extract is dried over magnesium sulphate (10 g.), made up to 550 cc. by adding toluene and then hydrogenated in the presence of a catalyst (200 mg.) consisting of palladium deposited on charcoal, containing 10% of palladium metal.

The hydrogenation is carried out at 85° – 90°C under a pressure of hydrogen equal to 800 mm of water. After 3 hours 40 minutes, absorption is complete. The mixture is then heated at the reflux temperature of toluene and a hot filtration is effected to remove the catalyst. The filtrate is cooled slowly to ambient temperature, and then in ice. The trimethyl-hydroquinone which has precipitated is filtered off and washed with chilled hexane (3 times 40 cc.).

After draining and drying in vacuo for 3 hours, white trimethyl-hydroquinone (20.3 g.) is obtained, the elementary analysis of which is in agreement with theory. The yield is 72.6%.

A polarographic determination is carried out on the combined organic phases; they are found to contain a further 450 mg. of trimethyl-hydroquinone. The overall yield is 74.2%.

Various types of analyses are carried out on the isolated trimethyl-hydroquinone which is in the form of white crystals: polarographic determination: 100%, microanalysis in agreement with theory, melting point: 174°C and UV index: $E_{1\ cm}^{1\%}$ in ethanol at 290 nm = 205.5.

EXAMPLE 3

A 15% strength aqueous solution (100 cc.) of sulphuric acid (0.15 mol) and pyrolusite (11 g.) (0.11 mol of $MnO_2$) are introduced into the same type of apparatus as in Example 2.

The mixture is heated to 70°–75°C, with stirring, and molten 2,3,6-trimethyl-phenol (6.7 g.; 0.049 mol) and pure sulphuric acid (10 g.; 0.1 mol) dissolved in water (10 cc.) are run in simultaneously. The running-in process is carried out over the course of 40 minutes; heating at 70°C is continued for 25 minutes and then the mixture is allowed to cool to ambient temperature.

The reaction mixture is filtered, the precipitate is washed with methyl isobutyl ketone (3 times 50 cc.) and the filtrate is extracted with methyl isobutyl ketone (3 times 50 cc.). The combined organic phases are made up to 500 cc.

After reducing a portion of this liquid by means of zinc in an acid medium, trimethyl-hydroquinone (corresponding to a weight of 6.05 g.) is determined by polarography.

The yield of the reaction is 80.8%.

EXAMPLE 4

Natural manganese dioxide (11 g.; 0.11 mol) and a 30% strength aqueous solution (100 cc.) of sulphuric acid (0.306 mol) are introduced into the same type of apparatus as in Example 2, and 2,3,6-trimethyl-phenol (6.8 g.; 0.05 mol) is added in small portions, with stirring, over the course of 2 hours 40 minutes. The temperature of the reaction mixture does not exceed 25°C. When the addition of 2,3,6-trimethyl-phenol is complete, stirring is continued for a further 2 hours at this same temperature.

The reaction mixture is then filtered and the precipitate is washed with methyl isobutyl ketone (3 times 30 cc.). The aqueous filtrate is extracted with methyl isobutyl ketone (4 times 80 cc.).

The organic phases are combined and made up to 500 cc. by adding the same solvent, and after reduction as in Example 3, 5.7 g. of trimethyl-hydroquinone is obtained; this represents a yield of 76% relative to the 2,3,6-trimethyl-phenol.

I claim:

1. Process for the preparation of trimethyl-benzoquinone which comprises oxidising 2,3,6-trimethylphenol directly with manganese dioxide in an aqueous solution containing sulphuric acid in an amount up to 40% by weight at a temperature from 10°C up to the reflux temperature of the reaction mixture, at least 1 mol of sulphuric acid being present per mol of manganese dioxide.

2. Process according to claim 1, in which the concentration of sulphuric acid is 5 to 30% by weight.

3. Process according to claim 1 in which the molar ratio of manganese dioxide to 2,3,6-trimethyl-phenol is from 1.8 to 3.

4. Process according to claim 3, in which the molar ratio of manganese dioxide to 2,3,6-trimethyl-phenol is from 2.1 to 2.5.

5. Process according to claim 1 in which the sulphuric acid is present in an amount from 1 to 4 mols per mol of manganese dioxide.

6. Process according to claim 5, in which the sulphuric acid is present in an amount of about 2 mols per mol of manganese dioxide.

7. Process according to claim 1, in which the oxidation is effected at a temperature from 20° to 80°C.

8. Process according to claim 1 in which the oxidation is carried out by introducing 2,3,6-trimethylphenol into the aqueous solution of sulphuric acid containing manganese dioxide in suspension.

9. Process according to claim 1 which comprises oxidising 2,3,6-trimethyl-phenol with manganese dioxide in an aqueous solution containing 5 to 30% by weight of sulphuric acid at a temperature from 10°C to the reflux temperature of the reaction mixture, the molar ratio of manganese dioxide to 2,3,6-trimethylphenol being from 1.8 to 3 and 1 to 4 mols of sulphuric acid being present per mol of manganese dioxide.

\* \* \* \* \*